United States Patent

Dunbar et al.

[11] 3,948,286
[45] Apr. 6, 1976

[54] ROTARY VALVE FOR AN OXYGEN GENERATOR

[75] Inventors: Jack E. Dunbar; Richard W. Hradek, both of Davenport, Iowa

[73] Assignee: The Bendix Corporation, South Bend, Ind.

[22] Filed: Dec. 13, 1974

[21] Appl. No.: 532,668

[52] U.S. Cl. ........... 137/609; 137/613; 137/625.21; 137/628
[51] Int. Cl.² ......................................... F16K 11/02
[58] Field of Search ....... 137/625.21, 628, 613, 609

[56] References Cited
UNITED STATES PATENTS

| | | | |
|---|---|---|---|
| 1,055,781 | 3/1913 | Mitchell et al................. | 137/625.21 |
| 2,079,041 | 5/1937 | Ryan et al...................... | 137/625.21 |
| 3,621,879 | 11/1974 | Ticcioni............................. | 137/613 |
| 3,746,048 | 7/1973 | Harper.............................. | 137/628 |

FOREIGN PATENTS OR APPLICATIONS

| | | | |
|---|---|---|---|
| 331,916 | 10/1903 | France............................ | 137/625.21 |
| 451,660 | 4/1913 | France............................ | 137/625.21 |

*Primary Examiner*—William R. Cline
*Assistant Examiner*—H. Jay Spiegel
*Attorney, Agent, or Firm*—Leo H. McCormick, Jr.; William N. Antonis

[57] ABSTRACT

A breathing system control valve having a housing with a distribution chamber therein which communicates with a source of air under pressure. A shaft which extends into the distribution chamber engages a plurality of discs and is operatively connected to a motor which provides the shaft with a rotative torque to alternately communicate air under pressure through a portion of the discs to either a first chamber or a second chamber wherein an oxygen enriched product effluent is developed while another portion of the discs allows a purge fluid from the other of the first and second chambers to escape to the atmosphere. Prior to the transfer of the air under pressure from one of the first and second chambers to the other, an equalization passage is opened to permit communication therebetween to establish a rapid operational build-up of air under pressure.

15 Claims, 7 Drawing Figures

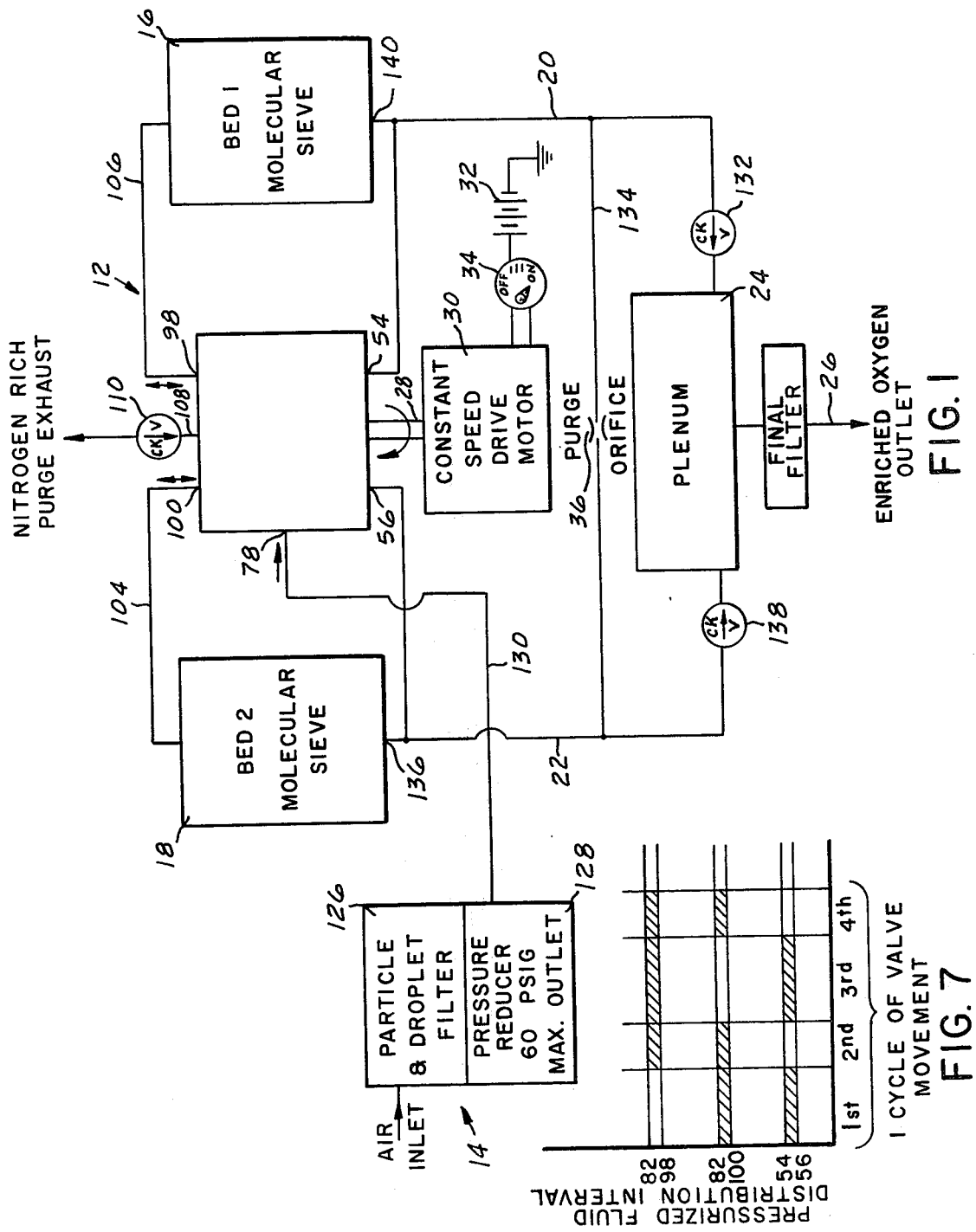

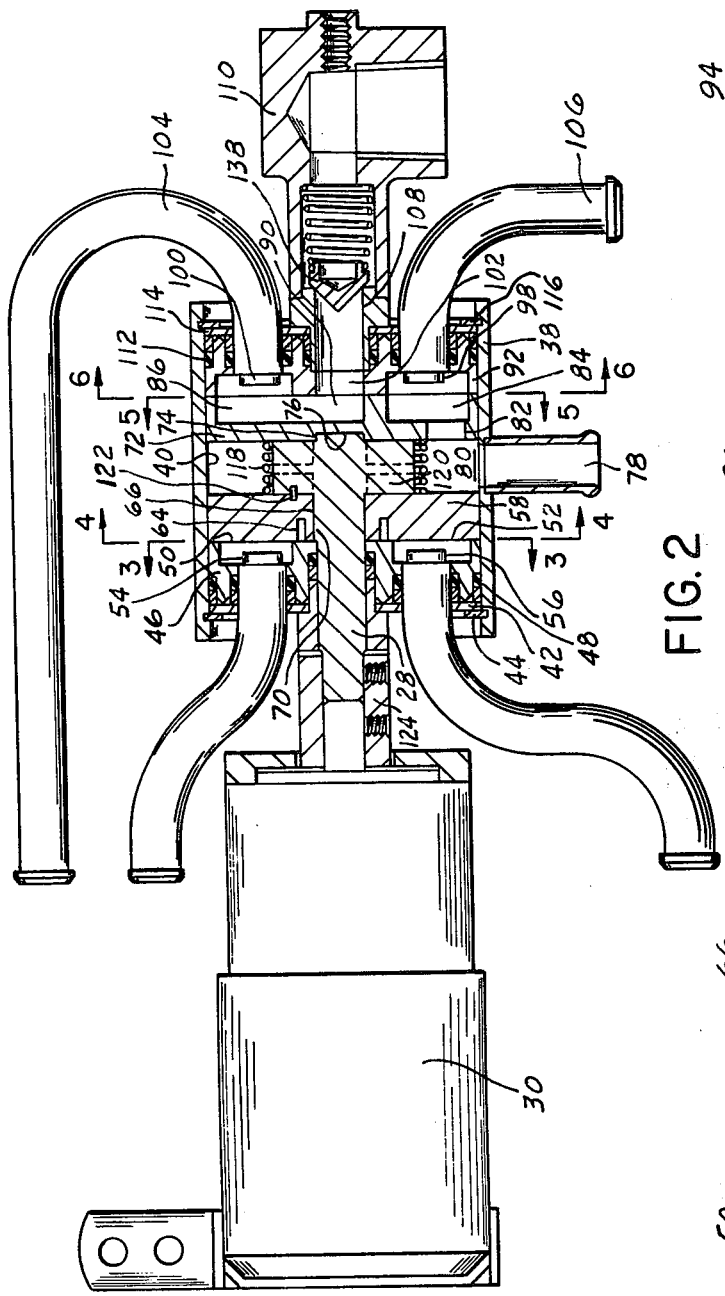
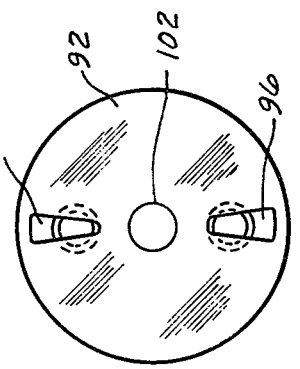
FIG. 6
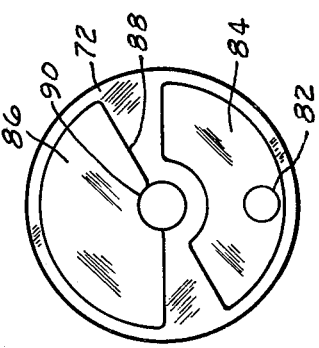
FIG. 5
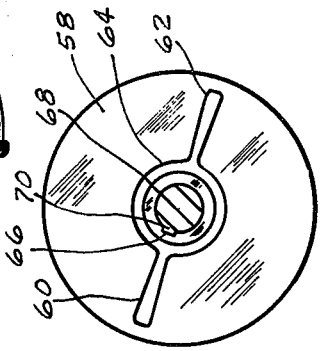
FIG. 4
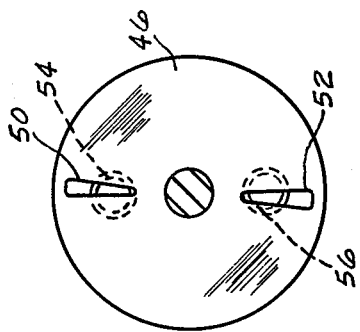
FIG. 3

ROTARY VALVE FOR AN OXYGEN GENERATOR

BACKGROUND OF THE INVENTION

Air can be fractionalized by removing various components thereof through the affinity of these components with various molecular sieve materials. Apparatus for fractionalization can be found in U.S. Pat. Nos. 2,944,627, 3,280,536 and 3,142,547. In these cases, air under pressure is communicated to containers holding the molecular sieve material. It has been found that a molecular sieve material having an Angstrom pore size of 5 will continually produce an oxygen enriched effluent by the so-called pressure swing technique. In the above referred to patents, in achieving the proper flow of the air and oxygen enriched effluent for the pressure swing technique, a plurality of control valves are located in the supply conduit and the output conduit. The operation of the control valves are usually controlled by a timer to develop the maximum efficiency for the desired oxygen concentration in the enriched effluent. Because of the presence of inert gases in air the maximum concentration achievable will be 96%.

SUMMARY OF THE INVENTION

We have devised a control valve for use in a breathing system utilizing the pressure swing technique of concentrating oxygen to sequentially present air under pressure to a plurality of beds of molecular sieve material and distribute a purge fluid to the atmosphere to achieve an efficient operation.

The control valve has a housing with a plurality of distribution ports for sequentially communicating air under pressure to a corresponding plurality of beds each containing a molecular sieve material to develop the oxygen enriched effluent. The output conduits of beds of molecular sieve material are interconnected to each other to permit a portion of the oxygen enriched effluent to flow through another bed and remove nitrogen retained thereon. A first disc means having sequential openings is located in the housing adjacent the distribution ports. A second disc means has an inlet port for supplying the air under pressure to a single distribution port at one time and an exhaust passage for transmitting the purge product from another distribution port to the atmosphere. Third and fourth discs located in the housing have openings therein to establish an equalization flow path between the plurality of chambers prior to the transmission of air under pressure through the inlet port. A rotary means is connected to the second disc and the third disc to provide an angular rotation to sequentially allow air under pressure to be communicated to the plurality of beds containing the molecular sieve material.

It is therefore the object of this invention to provide a breathing system with a control valve responsive to a rotary means for selectively supplying one bed of a plurality of beds, each of which contain a molecular sieve material, with air under pressure while simultaneously permitting a purge fluid to be communicated from another bed to the atmosphere to provide a continuous output of an oxygen enriched product effluent.

It is another object of this invention to provide a control valve with a rotary means which selectively permits air to flow to a first bed of molecular sieve material while simultaneously allowing a purge fluid to flow from a second bed of molecular sieve material in a first mode of operation, which allows the pressure of air in the first bed and the second bed to be equalized in a second mode of operation, which permits air to flow to the second bed and the purge fluid to flow from the first bed in a third mode of operation, and which allows the pressure of the air in the second bed and the first bed to be equalized in a fourth mode of operation during a single cycle of operation.

It is still a further object of this invention to provide a control valve responsive to rotation to control the supply of air and the release of a purge effluent in a pressure swing oxygen generator.

These and other objects will be apparent to those who read this specification and view the drawing.

BRIEF DESCRIPTION OF THE DRAWING

FIG. 1 is a schematic illustration of a breathing system having a rotary control means for regulating the flow of air under pressure to a plurality of beds of molecular sieve material to continually produce a supply of oxygen enriched breathable fluid.

FIG. 2 is a sectional view of the rotary valve of FIG. 1.

FIG. 3 is a sectional view taken along line 3—3 of FIG. 2 showing a control disc which provides for pressure equalization between the first bed and the second bed of molecular material in the system of FIG. 1.

FIG. 4 is a sectional view taken along line 4—4 of FIG. 2 showing timing disc which is mated to the control disc in FIG. 3 to allow the pressure equalization to take place during a set sequence in the pressure swing operation.

FIG. 5 is a sectional view taken along line 5—5 of FIG. 2 showing a disc for segregating the flow of air to one of the beds of molecular sieve material while allowing the flow of the purge fluid from the other bed in FIG. 1 during a cycle of the rotary valve in FIG. 2.

FIG. 6 is a sectional view taken along lines 6—6 of FIG. 2 showing a distribution disc for transmitting air under pressure to first bed and second bed and the purge fluid to the atmosphere.

FIG. 7 is a graph showing the flow distribution of the air under pressure during a cycle of rotation of the motor.

DETAILED DESCRIPTION OF THE PREFERRED EMBODIMENT

The breathing system 10 shown in FIG. 1 has a control valve 12 which sequentially presents air under pressure from source 14 to a first chamber 16 and a second chamber 18 from which a product effluent rich in oxygen which is produced and transmitted through conduit 20 into a storage chamber or plenum 24 before being presented to a recipient through conduit 26. The control valve 12 is connected by shaft 28 to an electric motor 30. The electric motor 30 is connected to an electric power source 32 through a switch 34. The electric motor 30 will provide a rotary torque which will rotate the control valve 12 through which air under pressure is sequentially presented to either the first chamber 16 or the second chamber 18 and while a portion of the product effluent supplied to the storage chamber 24 is communicated through valve or orifice 36 to purge either the second chamber 18 or the first chamber 16 of residue adsorbed by the molecular sieve material in producing the product effluent. The control means will cycle from the first chamber 16 to the second chamber 18 in a direct relationship with the speed at which the electric motor 30 turns the shaft 28. During the shift of operation from the first chamber 16 to the second chamber 18, the control means will provide for equalization of the air pressure between the beds of molecular sieve material retained in each chamber. The molecular sieve material in each chamber in this breathing system will have a nominal pore size of 5 Angstroms which is sufficient for the adsorption of nitrogen from the air to produce the oxygen enriched product effluent used by a recipient.

The control valve 12 which controls the operation of the enrichment of the oxygen in the breathable air supply is shown in more particular detail in FIG. 2.

The control valve 12 has a housing 38 with bore 40 therethrough. A first end plate 42 is retained in the bore 40 by a snap ring 44. A first disc 46 fixed in the bore 40 adjacent the first end plate 42 has a seal 48 which prevents communication between the atmosphere and the bore 40. The first disc or restrictive disc 46 has a first equalization opening 50 and a second equalization opening 52 therein to restrict the size of the equalization ports 54 and 56. A second disc or bypass 58 has a first radial groove 60 and a second radial groove 62 which extend from a circular groove 64, see FIG. 4. A slot 66 located along the axial opening 68 engages a key 70 on shaft 78 to locate the second disc 58 with respect to a third disc 72. The third disc or distribution disc 72 has a rectangular opening 74 into which head 76 on shaft 28 is located to provide proper alignment with the second disc 58. An entrance port 78 in the housing 38 directs air under pressure from source 14 into a pressure chamber 80 which is formed between the second disc 58 and the third disc 72. The third disc has an inlet port 82, see FIG. 5, which extends into a first pressurizing opening 84 which is separated from an exhaust opening 86 by a divider wall 88. The exhaust opening or groove 86 extends into an axial opening 90. A fourth disc or control 92 adjacent the third disc 72 has a first distribution opening 94 and a second distribution opening 96 which restricts the flow of air from the pressurization opening 84 into a first distribution port 98 and a second distribution port 100 after a first rotation. The first distribution port 98 is connected to the first chamber 16 which contains the first bed of molcular sieve material by conduit 106. The second distribution port 100 is connected to the second chamber 18 which contains the second bed of molecular sieve material by conduit 104. The fourth disc or restriction 92 has an axial opening 102 which extends from axial opening 90 to an exhaust port 108. A check valve 110 is located in the exhaust port 108 for controlling communication between the atmosphere and the exhaust port 108. A seal 112 is located between the fourth disc 92 and a second end plate 114 to prevent communication between bore 40 and the atmosphere. A snap ring 116 is located in the housing 38 to hold the end plate in place. A spring or resilient means 118 located in the pressure chamber 80 in conjunction with the pressurized fluid urges the second disc 58 into seating engagement with the first disc 46 and the third disc 72 into a seating engagement with the fourth disc 92. The tee-shaped head 120 on the shaft 28 can be equipped with an aligning pin 122 for further engagement with the second disc 58 or mated with raised portions on the second and third discs. The shaft 28 is connected to the electric motor 30 by coupling 124.

MODE OF OPERATION OF THE PREFERRED EMBODIMENT

Upon experiencing a need for oxygen enriched breathing fluid an operator in an aircraft will activate switch 34 to provide motor 30 with the electrical energy needed to rotate shaft 28 at a speed which will operate the breathing system to produce the oxygen concentration desired.

Air under presssure will flow through the particle filter 126 through a pressure reducer 128 into conduit 130 for presentation to the entrance port 78.

In a first angular rotation or mode of operation, for a 1st time interval, see FIG. 7, air under pressure present in the pressure chamber 80 will flow through the inlet port 82 into the pressurizing opening 84 and out the distribution port 98 through conduit 106 to the first chamber 16 where the molecular sieve material will retain the nitrogen and produce an oxygen enriched effluent which will flow in conduit 20 past check valve 132 into the supply chamber or plenum 24 for distribution through conduit 26 to the recipient. As the oxygen enriched effluent is flowing in conduit 20, a portion thereof will flow through the interconnecting conduit 134 past the purge or restrictive orifice 36 into conduit 22 for presentation to outlet 136 in the second chamber 18. The oxygen enriched effluent will flow through the second bed of molecular sieve material and desorb nitrogen therefrom before entering conduit 104 connected to the second distribution port 100. The purge effluent will flow past flow distribution opening 94 into the exhaust opening 86 through the axial openings 90 and 102 into the exhaust port 108 for distribution to the atmosphere after overcoming the resiliently held poppet 138 of the check valve 110.

When the motor 30 has rotated the third or distribution disc 72 through an angle equal to the pressurizing opening 84, divider wall 88 will seal the distribution ports 98 and 100. At the same time, the first and second radial slots 60 and 62, respectively, of disc 58 will be moved to open the equalization ports 50 and 52 of disc 46 to establish a second mode of operation for a 2nd time interval, see FIG. 7, through the angular rotation of shaft 28. With the equalization ports 50 and 52 in communication the pressure of the air and product effluent in the first bed will be equal to that in the second bed.

Further rotation of the second disc 58 and third disc 72 will again seal the equalization ports 50 and 52 and bring the pressurizing opening 84 into communication with the second distribution port 100 to allow air under pressure to flow through the inlet port 82 to the second chamber 18 where the molecular sieve material will adsorb nitrogen to produce an oxygen enriched product effluent. The oxygen enriched product effluent will flow through conduit 22 past check valve 138 into the storage chamber 24. A portion of the oxygen enriched product effluent will flow past the purge or restrictive orifice 36 into the outlet 140 of the first chamber 16. The purge effluent will desorb nitrogen in the first bed of molecular sieve material before passing through conduit 106 to distribution port 98. The purge effluent will flow past port segment 96 into the exhaust opening 86 through the axial bores 90 and 102 before exiting to the atmosphere through check valve 110 during a third mode of operation in a 3rd time interval, as illustrated in FIG. 7.

Further rotation of shaft 28 will move the divider wall 88 on the third disc 72 to seal the distribution ports 98 and 100 and to open the equalization ports 54 and 56 by the radial grooves 60 and 62 in the second disc 58 to establish equal pressure in the first and second chamber during a fourth mode of operation or angular rotation in a 4th time interval, see FIG. 7, to complete a single cycle of rotation by shaft 28.

Thus the entire presentation of the air under pressure is controlled by a single valve 12 to provide simplicity in the operation of this on-board oxygen generator for use in an aircraft.

We claim:

1. A fluid flow system comprising:

a first housing having a first chamber therein and a second chamber therein, said first chamber and said second chamber each containing a material which will produce a product effluent from a fluid, said first chamber and said second chamber being interconnected to each other and to a supply reservoir through a conduit means, control valve means having a second housing with a control chamber therein, said second housing having an entrance port connected to a supply of said fluid under pressure, a first distribution port connected to said first chamber, a second distribution port connected to said second chamber, a first equalization port connected to said first chamber, a second equalization port connected to said second chamber, and an exhaust port;

first disc means located in said control chamber on one side of said entrance port and having a first equalization opening adjacent the first equalization port and a second equalization opening adjacent the second equalization port;

second disc means located adjacent the first disc means and having a first equalization slot and a second equalization slot interconnected by a passage through which communication can occur between the first equalization port and the second equalization port;

third disc means located in said control chamber on the other side of said entrance port for defining a pressure chamber within said control chamber, said third disc means having a first pressurization opening and an exhaust opening therein on the side opposite said pressure chamber which extends into a first axial bore;

fourth disc means located adjacent said third disc means having a first distribution opening adjacent the first distribution port, a second distribution opening adjacent the second distribution port, and a second axial bore which connects said first axial bore with the exhaust port; and means extending through said first disc means for moving said second disc means and said third disc means to allow said fluid under presssure to flow through said first pressurization opening into said first distribution port for distribution to said first chamber where said product effluent is produced, a portion of which is communicated through said interconnecting conduit means to purge said second chamber by flowing through the second distribution port past the second distribution opening through the exhaust opening in the third disc means to the axial bore through the exhaust port to the surrounding environment during a first angle of rotation, to prevent flow through said first and second distribution ports and bring the first and second equalization slots of the second disc means into alignment with the first and second equalization openings of the first disc means to allow the pressure of the fluid in said first and second chambers to equalize during a second angle of rotation, to allow said fluid to flow through the first pressurization opening into said second distribution port for distribution to said second chamber where said product effluent is produced, a portion of which is communicated through said interconnecting conduit means to purge said first chamber by flowing through the first distribution port past the first distribution opening through the exhaust opening in the third disc means to the axial bore and into the exhaust port to the surrounding environment during a third angle of rotation, and to prevent flow through the first and second distribution ports and bring the first and second equalization slots of the second disc means into alignment with the first and second equalization openings of the first disc means to allow the pressure of the fluid in said first and second chambers to equalize during a fourth angle of rotation to complete a single cycle of rotation.

2. The control valve, as recited in Claim 1, further including:

resilient means located in said pressure chamber for biasing the second disc means against the first disc means and the third disc means against the fourth disc means to establish a seal therebetween.

3. The control valve, as recited in claim 2, wherein said means for moving the second and third disc means includes:

shaft means which extends through the first disc means and the second disc means to engage the third disc means.

4. The control valve, as recited in claim 3, wherein said means for moving the second and third disc includes:

key means associated with the shaft means for positively locating the first and second slots in the second disc means with respect to the third slot and third segmental opening in the third disc means to establish the sequential operations during a single cycle of rotation of the shaft means.

5. The control valve, as recited in claim 4, further including:

check valve means located in said exhaust port for preventing contaminants from entering into said axial bore.

6. The control valve, as recited in claim 5, wherein said means for moving said second and third disc means further includes:

motor means connected to said shaft means for providing a torque with which to rotate the second disc means and the third disc means through repetitive cycles.

7. A breathing system wherein a product effluent having an oxygen concentration higher than air is produced comprising:

a first housing having a first chamber and a second chamber associated therewith, said first chamber and said second chamber each containing materials which will remove nitrogen from air flowing in a first direction to produce said product effluent and release nitrogen when a portion of said product effluent flows in a second direction;

control valve means having a second housing with a bore therein, said housing having an entrance port connecting said bore with a source of air under pressure, said housing having a first distribution port connecting said bore with said first chamber, said housing having a second distribution port connecting said bore with said second chamber, said housing having an exhaust port connecting said bore with the surrounding environment, passageway means associated with said second housing for connecting said first chamber with said second chamber;

distribution disc means located in said bore having a first distribution opening adjacent the first distribution port, a second distribution opening adjacent the second distribution port, and an axial opening in line with said exhaust port;

control disc means located in said bore between the distribution disc means and the entrance port having a surface adjacent the distribution disc means which separates the first distribution opening from the second distribution opening, said surface having a passage for connecting one of said first and second distribution openings with said axial opening, said control disc means having an inlet port connecting the entrance port with the other of said first and second distribution openings; and motor means connected to said control disc means for sequentially moving said inlet port relative to said distribution disc means to permit air under pressure to flow through the first distribution opening in said first direction to the first chamber to allow the product effluent to flow in said second direction from the second chamber through said second distribution port to said passage and out the exhaust port during a first time interval, to simultaneously interrupt the communication of the pressurized air in said first direction through said inlet port and the flow of the portion of said product effluent in said second direction through said passage and allow communication between said first chamber and said second chamber through said passageway means to equalize the pressure of the fluid therein during a second time interval, to permit air under pressure to flow in said first direction through said inlet port past the second distribution opening into the second chamber while the portion of said product effluent is flowing in said second direction from the first distribution opening into said passage during a third time interval, and again to simultaneously interrupt the communication of the flow of pressurized air in the first direction through said inlet port and the flow of the portion of said product effluent through said passage to the exhaust port to allow communication through said passageway means to equalize the pressure of the fluid in the first chamber and the second chamber during a fourth time interval to complete a single cycle.

8. The breathing system, as recited in claim 7, wherein said control valve means further includes:
equalization disc means located in said bore for separating said passageway means from said entrance port, said equalization disc means being connected to said motor means to sequentially establish communication between the first chamber and the second chamber during said second and fourth time intervals.

9. The control valve as recited in claim 7, wherein said control valve further includes:
check valve means attached to said housing for preventing contaminants from entering into the first chamber and the second chamber through the exhaust port.

10. The control valve, as recited in claim 7, wherein said passageway means includes:
a first equalization port in said second housing connected to said first chamber; and
a second equalization port in said second housing connected to said second chamber.

11. The control valve, as recited in claim 10, wherein said control valve means further includes:
bypass means attached to said means for moving the control disc having an interconnected first radial groove and second radial groove through which said fluid is communicated between said first and second equalization ports during the said second and fourth time intervals.

12. The control valve, as recited in claim 11, wherein said means for moving the control disc and the bypass disc includes:
shaft means which extends through said second housing having a key which engages said bypass disc means and a rectangular end for engaging said control disc means for sequentially aligning the first and second radial grooves with the first and second equalization ports and the input port and passage with the first and second distribution ports during said first, second, third and fourth periods of angular rotation.

13. The control valve, as recited in claim 12 wherein said rotary means further includes:
resilient means located in said bore for biasing the control disc means and the bypass disc means away from each other and toward the distribution disc means and said second housing, respectively, to assist said air under pressure in establishing a fluid tight seal therebetween.

14. The control valve, as recited in claim 13, further including:
first restrictive means associated with the first equalization port for limiting the duration of communication between the first chamber and the first and second radial grooves during the second and fourth time intervals; and
second restrictive means associated with the second equalization port for limiting the duration of communication between the second chamber and the second and first radial grooves during the second and fourth time intervals.

15. The control valve, as recited in claim 14, wherein said first and second restrictive means is a restrictive disc having a first restrictive opening and a second restrictive opening located therein for establishing the second and fourth time intervals.

* * * * *